United States Patent [19]

Login et al.

[11] Patent Number: 5,002,763

[45] Date of Patent: Mar. 26, 1991

[54] WATER SOLUBLE COMPLEXES OF POLYVINYLPYRROLIDONE, HYDROGEN CHLORIDE AND IODINE AND PROCESS FOR MAKING THE SAME

[75] Inventors: Robert B. Login, Oakland; John J. Merianos, Middletown, both of N.J.

[73] Assignee: GAF Chemicals Corporation, Wayne, N.J.

[21] Appl. No.: 501,459

[22] Filed: Mar. 30, 1990

Related U.S. Application Data

[62] Division of Ser. No. 347,648, May 5, 1989, Pat. No. 4,939,272.

[51] Int. Cl.$^5$ .............................................. A61K 31/79
[52] U.S. Cl. ..................................... 424/80; 524/401; 524/530; 424/667
[58] Field of Search ................... 524/401, 530; 424/80, 424/667

[56] References Cited

U.S. PATENT DOCUMENTS 2,754,245  7/1956  Hosmer ................................. 424/80
4,684,519  8/1987  Barabas ............................... 424/667

OTHER PUBLICATIONS

Schenck et al.–"Some Model Studies... Carriers" Apr. 79.

Primary Examiner—Thurman K. Page
Assistant Examiner—Peter F. Kulkosky
Attorney, Agent, or Firm—Walter Katz; Marilyn J. Maue; Joshua J. Ward

[57] ABSTRACT

A water soluble complex of polyvinylpyrrolidone, hydrogen chloride and iodine, and a process for making the same, is provided herein.

28 Claims, No Drawings

WATER SOLUBLE COMPLEXES OF POLYVINYLPYRROLIDONE, HYDROGEN CHLORIDE AND IODINE AND PROCESS FOR MAKING THE SAME

This is a division of application Ser. No. 347,648, filed May 5, 1989, now U.S. Pat. No. 4,939,272.

BACKBROUND OF THE INVENTION

1. Field of the Invention

This invention relates to complexed iodine products, and, more particularly, to water soluble complexes of polyvinylpyrrolidone, hydrogen chloride and iodine, and to a process for preparing such water soluble complexes as a stable, free-flowing powder having substantially all of its complexed iodine available for antibacterial activity.

2. Description of the Prior Art

Iodine or with metallic salts such as sodium or potassium iodide, known as Lugol's solution has been used as a disinfectant for nearly 150 years; however, its low solubility in water has required formulation in alcohol, known as "tincture of iodine". A water soluble form of iodine then was developed in which iodine was complexed with water soluble polyvinylpyrrolidone (PVP), which is an inert carrier. The PVP-$I_2$ complex, however, was not entirely satisfactory. In particular, during preparation of the complex, ⅓ of the iodine reactant was reduced to iodide ion which does not contribute to antimicrobial activity. Thus, the PVP-$I_2$ complex required 17.2% iodine reactant to produce a 10% active iodine product.

Accordingly, it has been desired to provide a water soluble complex of iodine having an increased available iodine content relative to the amount of iodine used for its preparation. Hosmer. W., in U.S. Pat. No. 2,754,245, issued July 10, 1956, thus provided a water soluble iodine monochloride adduct of polyvinylpyrrolidone by heating a mixture of the compounds. However, the total iodine used was 17.4% while available iodine was only Later, Schenck, H. et al., in an article in *Makromol. Chem.*, 181, 1871-1888 (1980), entitled "Some Model Studies on the Chemistry and Structure of Polyvinylpyrrolidone Halogen Carriers", described a solution process for the preparation of a water-insoluble complex of polyvinylpyrrolidone, hydrogen chloride and iodine. The process comprised mixing a solution of PVP in methanol with aqueous HCl and iodine, and drying the residue in a vacuum desiccator. The water insolubility property of this adduct, however, is disadvantageous for commercial use, where aqueous solutions are preferred formulations.

Schenck, H. et al., in the *J. Pharmaceutical Sciences* 68, No. 12, 1505-1509 (1979), entitled "Structure of Polyvinylpyrrolidone-Iodine (Povidone-Iodine)", attributed part of the water solubility of PVP-$I_2$ complexes to the appreciable number of free pyrrolidone moieties in the complex. Free pyrrolidone moieties are units of the PVP polymer which do not participate in complexation of $I_2$ present in the form of $I_3^-$ ions. More particularly, in the PVP-$I_2$ complex, 18 units of PVP are free while 2 units of PVP are utilized for complexation. The structure of the complex thus is an adduct of the PVP polymer and hydrogen triiodide in which a proton is fixed by hydrogen bonding between two carbonyl groups of two pyrrolidone rings, either vicinal or non-vicinal, and the triiodide anion is bound ionically to the hydrogen cation, as shown pictorially below:

STRUCTURE OF PVP-$I_2$ COMPLEX

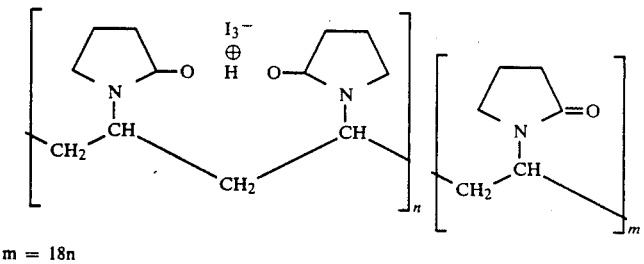

m = 18n

Apparently, the water-insoluble PVP/HCl/$I_2$ complex of Schenck did not possess the requisite free PVP units necessary to provide water solubility.

Accordingly, it is an object of this invention to provide a water soluble complex of PVP, HCl and $I_2$.

Another object herein is to provide a water soluble PVP/HCl/$I_2$ complex in which substantially all of the iodine therein is available for antimicrobial activity.

Still another object is to provide a water soluble PVP/HCl/$I_2$ complex which is a stable, non-toxic, free flowing, lightly colored, dry powder having effective antimicrobial activity.

Yet another object herein is to provide aqueous solutions of water soluble PVP/HCl/$I_2$ complexes which are stable, and skin insensitive, and show antimicrobial activity at iodine levels lower than that of commercial, complexed iodine products.

Another object of the invention is to provide a process for preparing water soluble complexes of PVP, HCl and $I_2$.

A particular object herein is to provide such a process in which a substantial number of free pyrrolidone units remain intact during preparation of the complex, and substantially all of the iodine reactant is complexed as available iodine.

These and other objects and features of the invention will be made apparent from the following more particular description of the invention.

SUMMARY OF THE INVENTION

A water soluble complex of polyvinylpyrrolidone, hydrogen chloride and iodine is provided herein. The molecular formula of the complex can be represented as (PVP)$_2$HCl:$I_2$. The water soluble complex of the invention is a stable, non-toxic, free flowing powder having about 1 to 20% available iodine, preferably about 5 to 10%. The available iodine within the complex is present predominantly in the form of $I_2Cl^-$ ions. PVP remains therein substantially in the form of free PVP units which provide water solubility for the complex.

The water soluble complexes of the invention are made by a dry powder process in which excess PVP powder is complexed with dry HCl gas, and then iodine is mixed therewith.

DETAILED DESCRIPTION OF THE INVENTION

1. Preparation of Water Soluble PVP/HCl/I$_2$ Complex

The water soluble polyvinylpyrrolidone/hydrogen chloride/iodine (PVP/HCl/I$_2$) complexes of the invention may be conveniently prepared in a one-pot, two-step process.

A. (PVP)$_2$HCl Complex

The first step of the process comprises forming an intermediate complex between excess PVP and HCl. The PVP component is present in a substantial excess over the 2 molar units necessary for complexation with HCl. The molecular weight of the PVP polymer is about 20,000 to 1,000,000, preferably about 40,000.

This reaction preferably is carried out by feeding dry HCl gas slowly through PVP powder at ambient temperatures. An exothermic reaction occurs upon contact of the gas and powder thus increasing the temperature of the reaction mixture about 10°–15° C. The gaseous HCl reactant preferably is introduced into a charge of PVP powder over a period of an hour or more, with adequate mixing, in order to control the exotherm of the reaction. The complexation reaction may be effected under reduced pressure, e.g. a mild vacuum of 90 mm is suitable. Atmospheric pressure also may be used.

The PVP/HCl complex produced is a white powder having a molar ratio of PVP (unit mole) to HCl of about 2:1 (14.12% by weight HCl for complete saturation), i.e. the formula of the complex is (PVP)$_2$HCl.

B. (PVP)$_2$HCl:I$_2$ Complex

The second step of the process involves addition of a predetermined amount of iodine to the (PVP)2HCl complex. This reaction is suitably carried out in situ under the same reaction conditions of ambient temperature and mild vacuum as in the first step. Substantially all of iodine introduced becomes available iodine in the PVP/HCl/I$_2$ complex. Generally, the amount of iodine reactant is calculated to produce about a 1–20% available iodine level in the complex, preferably about 5–10%, as determined by the thiosulfate-titratable iodine method.

The dark brown PVP/HCl/I$_2$ reaction product may be stabilized by heating to remove residual traces of free iodine present on the surface of the complex. Heating below 100° C., and, preferably, about 75°–90° C., for a few hours, is effective for this purpose. After the heat treatment, a water soluble, light brown, free flowing powder is obtained. The yield of the complex is substantially quantitative.

Substantially all the iodine used in forming the complex becomes available iodine; i.e. about 90% or more of iodine reactant remains as available iodine in the complex, and only 10% or less of the iodine reactant is converted to iodide ion, based upon total acidity of the complex less the HCl introduced. Accordingly, charged amounts of iodine will essentially determine the resultant available iodine levels in the complex, as shown in Table I below.

TABLE 1

| Charged I$_2$ (wt. %) | Available I$_2$ (wt. %) |
|---|---|
| 7.35 | 5.62 |
| 10.1 | 8.51 |
| 11.3 | 9.65 |
| 18.2 | 16.14 |

2. Properties of Water Soluble PVP/HCl/I$_2$ Complex

A. Water Solubility

The water solubility property of the complex of the invention enables aqueous solutions to be prepared therefrom. Complexes having low available iodine levels have higher water solubility. The water solubility of complexes with a 5% available iodine level is 20 g/100 ml., at 10% available iodine it is 14 g/100 ml., and at 15% available iodine it is 9 g/100 ml. Accordingly, a complex having about 1 to 20% available iodine provides particularly useful complexes having excellent water solubility properties.

The water solubility property of the complex of the invention can be attributed to a substantial percentage therein of water soluble, free PVP units among all PVP units. Such free PVP units provide water solubility, whereas complexed PVP units, and hydrolyzed and cross-linked PVP units, are water-insoluble. In the complex herein, it is believed that for each 20 molar units of PVP in the water soluble complex, only two are used for complexation with HCl and I$_2$, while 18 molar PVP units remain free for water solubilization of the entire complex.

B. Composition and Structure of Complex

The molar formula of the complex can be represented as:

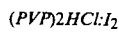

(PVP)2HCl:I$_2$ which reprsents a ratio of 2 complexed PVP molar units per mole HCl, and a 1:1 HCl to I$_2$ ratio, in a carrier of free PVP polymer units. The composition of the complex comprises 20% or less of iodine, 3% or less of HCl and 77% or more of complexed PVP; preferably about 5–10% iodine, 0.7 to 1.45% HCl and 88–94% complexed PVP, by weight.

The iodine in the solid complex has been determined by Raman resonance spectroscopy to be present at at 170 cm$^{-1}$. Accordingly, the structure of the complex of the invention is believed to be the following:

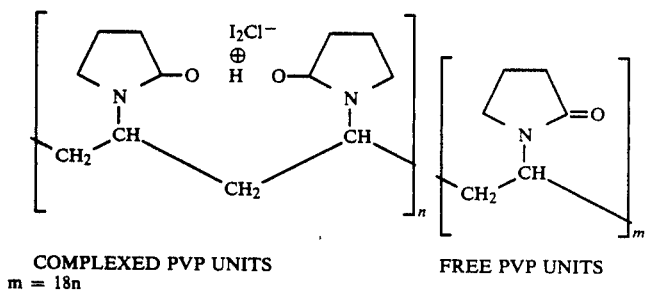

COMPLEXED PVP UNITS    FREE PVP UNITS
m = 18n

C. Antibacterial Formulations and Germicidal Activity

The water soluble powder complexes of the invention are capable of releasing iodine slowly to provide long lasting disinfectant action, of being non-toxic, non-foaming and non-irritating, and of requiring less iodine reactant to achieve the same level of antimicrobial activity, as compared to PVP-$I_2$. The complex of the invention is useful as a germicidal handwash, surgical scrubs, pre-operative preparation solutions, opthalmic formulations, bovine teat dips, sanitizer for the food and dairy industries, and disinfectant for drinking water.

A mini-version (10 carriers) of the use-dilution method* was used to confirm the germicidal activity of the complex in a buffered solution (pH of 4.5) at 50 ppm against Gram positive bacteria and at 150 ppm against Gram negative bacteria*. These results are expected since Gram negative bacteria are known to be more difficult to kill.

*Official Methods of Analysis of the AOAC, 14th Ed., 1984 Ch. 4, Disinfectants paragraph 4.007-4.0011
**Staphylococcus aureus ATCC No. 6538
***Salmonella choleraesuis ATCC No. 10708, and Pseudomonas aeruginosa PRD 10, ATCC No. 15442

D. Other Properties

1. Partition Coefficient

The complex has a partition coefficient of less than 20, as determined in the usual manner known in the art as in the method given in U.S. Pat. No. 3,028,300, which indicates that aqueous solutions of the complex, in contrast to the powder itself, will release iodine quickly for rapid disinfectant action.

2. Heat Stability

The heat stability of the complex in water solution (10% solid, 1% available iodine) at pH 2-3 was measured at 75° C. after 6 hours; only 2.5-3.5% of the available iodine was lost.

3. Free Iodine Content

The free iodine content of the complex is less than about 5 ppm.

The invention will be described more particularly by reference to the following examples.

EXAMPLE 1

A rotary blender was charged with 85.23 g. of PVP-CI dry powder (GAF Corp., K = 30) and evacuated with house vacuum (90 mm Hg). Then 2.06 g. of dry HCl gas was introduced slowly with mixing over a period of an hour at room temperature to produce a white powder. The 10°-15° C. exotherm of the reaction was controlled by the rate of gas and degree of mixing. Thereafter, 12.71 g. of iodine was added to the white powder which turned dark brown immediately; upon heating the dark brown powder to 90° C. for 6 hours, 100 g. of a light brown, water soluble PVP/HCl/$I_2$ complex was obtained in substantially quantitative yield. The available iodine content of the product was 11.44%. The complex was water soluble to the extent of 15 g/100 ml. Raman resonance spectroscopy showed a band at about 170 cm$^{-1}$ attributable to the presence of the $I_2Cl^-$ ion in the complex.

EXAMPLES 2-6

The process of Example 1 was repeated using the following charged amounts of PVP, HCl and $I_2$, to produce complexes of the composition represented by the amounts of reactants charged. In all compositions, less than 3% by weight of HCl is present in the complex.

TABLE 2

| | COMPOSITION OF COMPLEX | | | |
|---|---|---|---|---|
| | Charge (% by Wt.) | | | Determined |
| Ex. No. | PVP | HCl | $I_2$ | Available $I_2$ |
| 2 | 94.72 | 0.66 | 4.61 | 4.12 |
| 3 | 90.85 | 1.15 | 8.00 | 7.15 |
| 4 | 87.89 | 1.52 | 10.58 | 9.23 |
| 5 | 82.09 | 2.25 | 15.65 | 14.31 |
| 6 | 77.47 | 2.83 | 19.70 | 18.12 |

EXAMPLE 7

The procedure of Example 1 was repeated without the heat treatment step and using 88.4 g. of PVP, 1.47 g. of dry HCl gas and 10.1 g. of iodine. The product had 8.51 g. of available iodine in the complex.

EXAMPLE 8

Aqueous solutions (1%) of the complexes of Ex. 1-7 were prepared. The pH of the solutions was between about 2-3. The solutions taken were buffered with sodium phosphate to a pH of 4.5-5.5 and these test solutions were tested by the use-dilution method against Gram positive and Gram negative bacteria. The results indicated effective germicidal activity.

While the invention has been described with reference to certan embodiments thereof, it will be understood that changes and modifications may be made which are within the skill of the art.

What is claimed is:

1. An aqueous solution of the water soluble complex of PVP, HCl and $I_2$ which complex is a stable, free flowing powder in which the PVP is present in the complex substantially as free PVP molar units, the ratio of complexed PVP molar units to HCl is 2:1, and the molar ratio of HCl to $I_2$ is 1:1 formed by adding said powder to aqueous solvent.

2. An aqueous solution according to claim 1 in which the complex has the formula $(PVP)_2HCl:I_2$.

3. An aqueous solution according to claim 1 in which the iodine is present in the complex at least in part in the form of the $I_2Cl^-$ ion, which has a Raman resonance spectral band at about 170 cm$^{-1}$.

4. An aqueous solution according to claim 1 having about 1 to 20% by weight available iodine.

5. An aqueous solution according to claim 1 which has about 5 to 10% by weight available iodine.

6. An aqueous solution according to claim 4 having a pH of about 2 to 3.

7. An aqueous solution according to claim 1 comprising about 20% by weight or less of iodine, about 3% by weight or less of HCl and about 77% by weight or more of complexed PVP.

8. An aqueous solution according to claim 1 comprising about 5-10% iodine, about 0.7-1.45% HCl and about 85-94% complexed PVP.

9. A buffered aqueous solution of the water soluble complex of claim 1 having a pH of about 4.5-5.5.

10. A buffered aqueous solution of the water soluble complex of claim 7 having a pH of about 4.5-5.5.

11. A buffered aqueous solution of the water soluble complex of claim 8 having a pH of about 4.5-5.5.

12. An aqueous solution according to claim 1 which solution is capable of releasing iodine rapidly.

13. A process of making a water soluble $PVP/HCl/I_2$ complex comprising complexing a predetermined amount of dry PVP powder with gaseous HCl to form a $(PVP)_2$:HCl intermediate complex powder having a substantial number of free PVP molar units therein, and then reacting iodine therewith.

14. A process according to claim 13 wherein said both steps are carried out in situ.

15. A process according to claim 13 wherein both steps are carried out at ambient temperature.

16. A process according to claim 13 wherein both steps are carried out at reduced pressures.

17. A process according to claim 13 wherein dry HCl gas is introduced slowly into stirred PVP powder to control the exothermic reaction.

18. A process according to claim 13 wherein the iodine reactant provides a complex having about 1-20% available iodine.

19. A process according to claim 18 wherein said amount of iodine provides a complex having about 5-10% available iodine.

20. A process according to claim 13 including the step of heating the product to below 100° C.

21. A process according to claim 13 wherein about 77% by weight or more of PVP, about 3% by weight or less of HCl and about 20% by weight or less of iodine is used.

22. A process according to claim 21 wherein about 85-94% PVP, about 0.7-1.45% HCl and about 5-10% iodine is used.

23. A dry process for preparing a water soluble $PVP/HCl/I_2$, complex which comprises contacting a powder of a PVP-HCl complex having a substantial number of free PVP molar units therein with a predetermined amount of iodine.

24. A dry process according to claim 23 wherein the predetermined amount of iodine reactant provides a complex having about 1-20% available iodine.

25. A dry process according to claim 23 wherein said amount of iodine provides a complex having about 5-10% available iodine.

26. A dry process according to claim 23 including the additional step of heating the product to below 100° C.

27. A dry process according to claim 23 wherein the PVP-HCl complex has about 77% by weight or more of PVP and about 3% by weight or less of HCl and the iodine is about 20% by weight or less.

28. A dry process according to claim 27 wherein the resultant water soluble $PVP/HCl/I_2$ complex has about 85-94% PVP, about 0.7-1.45% HCl and about 5-10% iodine.

* * * * *